United States Patent [19]

Stöhr et al.

[11] Patent Number: 5,786,459
[45] Date of Patent: Jul. 28, 1998

[54] TETRAZO DYESTUFFS

[75] Inventors: Frank-Michael Stöhr; Peter Wild, both of Odenthal, Germany

[73] Assignee: Bayer Aktiengesellschaft, Leverkusen, Germany

[21] Appl. No.: 676,021

[22] Filed: Jul. 5, 1996

[30] Foreign Application Priority Data

Jul. 14, 1995 [DE] Germany ......................... 195 25 613.1
Aug. 17, 1995 [DE] Germany ......................... 195 30 202.8

[51] Int. Cl.$^6$ ................... C09B 35/031; C09B 35/233; C09D 11/02; D06P 1/04; D06P 1/39; D06P 1/41
[52] U.S. Cl. .................. 534/797; 534/796; 534/803; 106/31.27; 106/31.48; 106/31.51; 106/31.52
[58] Field of Search .................... 534/796, 797, 534/803; 106/31.27, 31.48, 31.51, 31.52

[56] References Cited

U.S. PATENT DOCUMENTS

| | | | |
|---|---|---|---|
| 2,258,977 | 10/1941 | Dickey et al. | 534/797 X |
| 3,072,454 | 1/1963 | Long et al. | 534/797 X |
| 3,108,846 | 10/1963 | Utsunomiya et al. | 534/797 X |
| 4,273,707 | 6/1981 | Pedrazzi | 534/797 |
| 4,465,627 | 8/1984 | Pedrazzi | 534/796 X |
| 4,594,410 | 6/1986 | Pedrazzi | 534/701 |
| 5,053,495 | 10/1991 | Greenwood et al. | 534/829 |
| 5,489,671 | 2/1996 | Ogino et al. | 534/664 |

FOREIGN PATENT DOCUMENTS

| | | | |
|---|---|---|---|
| 0190586 | 8/1986 | European Pat. Off. | 534/664 |
| 0356080 | 2/1990 | European Pat. Off. | 534/829 |
| 0645434 | 3/1995 | European Pat. Off. | 534/644 |
| 2378069 | 8/1978 | France | 534/664 |
| 2424305 | 11/1979 | France | 534/664 |
| 1298659 | 7/1969 | Germany | 534/797 |
| 63-105065 | 5/1988 | Japan | 534/797 |
| 64-106272 | 5/1989 | Japan | 534/797 |
| 1153775 | 6/1989 | Japan | 534/664 |
| 1197580 | 8/1989 | Japan | 534/664 |
| 2019873 | 11/1979 | United Kingdom | 534/664 |
| 1558307 | 12/1979 | United Kingdom | 534/664 |
| 2082615 | 3/1982 | United Kingdom | 534/664 |
| 2266893 | 11/1993 | United Kingdom | 534/664 |

Primary Examiner—Floyd D. Higel
Attorney, Agent, or Firm—Sprung Kramer Schaefer & Briscoe

[57] ABSTRACT

Compounds of the formula (I)

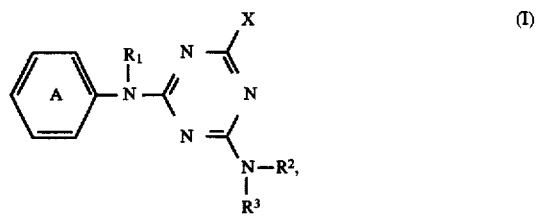

have been found which are suitable for dyeing and printing hydroxyl- and/or amido-containing substrates, in particular for printing paper by the ink-jet method.

12 Claims, No Drawings

TETRAZO DYESTUFFS

The invention relates to novel polyazo dyestuffs, to a process for their preparation and to their use for dyeing and printing hydroxyl- and/or amido-containing substrates, in particular for printing paper by the ink-jet method.

JP-A-1,197,580 and JP-A-1,153,775 already disclose polyazo dyestuffs. However, these dyestuffs still have some disadvantages in practical application.

The present invention provides novel compounds of the formula (I)

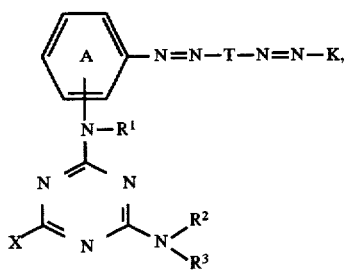

in which

- T represents the radical of a tetrazo component,
- K represents the radical of a coupling component,
- $R^1$ denotes hydrogen or substituted or unsubstituted $C_1$–$C_4$-alkyl,
- $R^2$ represents hydrogen or substituted or unsubstituted $C_1$–$C_4$-alkyl,
- $R^3$ denotes substituted or unsubstituted $C_1$–$C_4$-alkyl or
- $R^2$ and $R^3$ together with the N atom to which they are bonded form a saturated or unsaturated 3- to 8-membered, in particular 5- or 6-membered, ring which either does not contain any further heteroatoms or contains 1 to 2 further heteroatoms from the group consisting of O, S, SO, $SO_2$, NR, where R is H or substituted or unsubstituted $C_1$–$C_6$-alkyl, and is unsubstituted or substituted by $C_1$–$C_4$-alkyl, $C_1$–$C_4$-alkoxy, $C_1$–$C_4$-hydroxyalkyl or $C_1$–$C_4$-aminoalkyl,
- X represents OH, $C_1$–$C_4$-alkoxy, $C_1$–$C_4$-alkyl, $C_6$–$C_{10}$-aryl, mercapto, $C_1$–$C_4$-alkylmercapto or amino, in particular $NR^2R^3$ where $R^2$ and $R^3$ have the meaning given above, and ring A does, if desired, carry further substituents.

Preferred substitutents of alkyl groups are OH, $C_1$–$C_4$-alkoxy, halogen, such as Cl, F or Br, COOH, $SO_3H$, $OSO_3H$ and/or $NR^4R^5$ where $R^4$ and $R^5$, independently of one another, represent hydrogen or alkyl, in particular $C_1$–$C_4$-alkyl, which is unsubstituted or substituted by water-solubilizing groups.

Water-solubilizing groups are understood as meaning, in particular, $SO_3H$, $OSO_3H$, COOH.

Further substituents for ring A preferably include: $C^1$–$C_4$-alkyl, $C_1$–$C_4$-alkoxy, halogen, OH, —S—$C_1$–$C_4$-alkyl, $NR^4R^5$ where $R^4$ and $R^5$ have the meaning given above, $SO_3H$, COOH, —$NR^1COC_1$–$C_4$-alkyl, —$NR^1COC_6$–$C_{10}$-aryl, —$NR^1$—$SO_2$—$C^1$–$C_4$-alkyl, $NR^1$—$SO_2$—$C_6$–$C_{10}$-aryl, —$NR^1CONH_2$, —$NR^1$—$COCH_2OH$, $NR^1COOC_1$–$C_4$-alkyl where $R^1$ has the meaning given above and $NR^2R^3$ where $NR^2R^3$ have the meaning given above for a heterocyclic ring.

Preferred compounds of the formula (I) are those in which K is a coupling component from the benzene or naphthalene series.

In a particularly preferred embodiment, K denotes a radical of the formula (II)

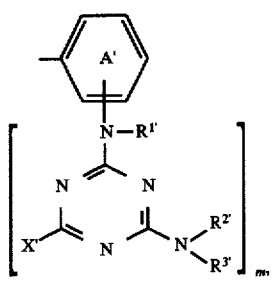

in which $R^{1'}$, $R^{2'}$, $R^{3'}$, X' and A' can adopt the meanings of the corresponding substituents $R^1$, R2, $R^3$, X and A but are different therefrom, and m represents 0 or 1.

If m is 0, the radical of the formula (II) is a radical of the formula (IIa)

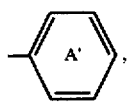

which preferably has one of the following meanings

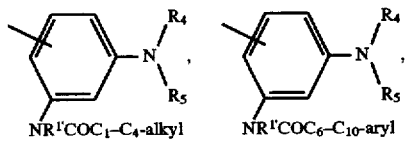 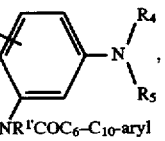

$NR^{1'}COC_1$–$C_4$-alkyl    $NR^{1'}COC_6$–$C_{10}$-aryl

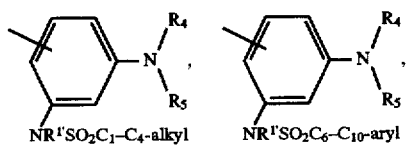 

$NR^{1'}SO_2C_1$–$C_4$-alkyl    $NR^{1'}SO_2C_6$–$C_{10}$-aryl

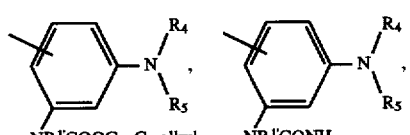 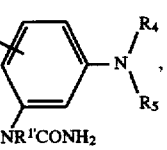

$NR^{1'}COOC_1$–$C_4$-alkyl    $NR^{1'}CONH_2$

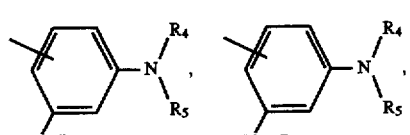 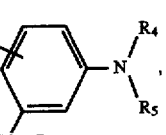

$NR^{1'}COCH_2OH$

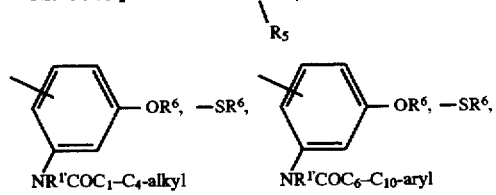 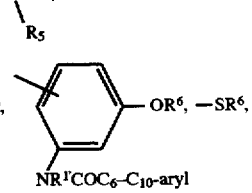

$NR^{1'}COC_1$–$C_4$-alkyl    $NR^{1'}COC_6$–$C_{10}$-aryl

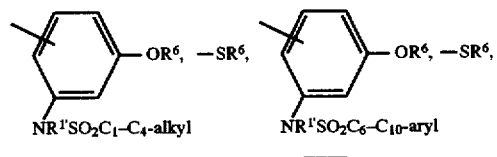 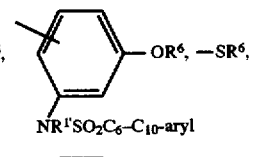

$NR^{1'}SO_2C_1$–$C_4$-alkyl    $NR^{1'}SO_2C_6$–$C_{10}$-aryl

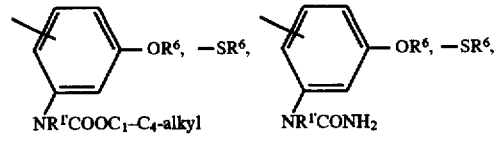 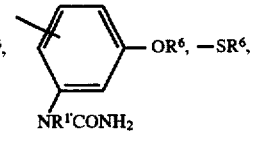

$NR^{1'}COOC_1$–$C_4$-alkyl    $NR^{1'}CONH_2$

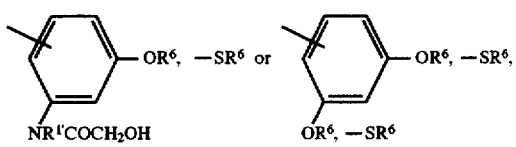

in which

R$^{1'}$, R$^4$ and R$^5$ have the meaning given above and R$^6$ can adopt the meanings of R$^{1'}$, but R$^6$ and R$^{1'}$ are independent from one another, and aromatic rings A' can, if desired, additionally carry further substituents from the series consisting of C$_1$–C$_4$-alkyl, C$_1$–C$_4$-alkoxy, halogen, in particular Cl, Br and F, SO$_3$H and/or COOH.

Examples of the radicals of the formula (II) where m is 0 include the following preferred compounds:

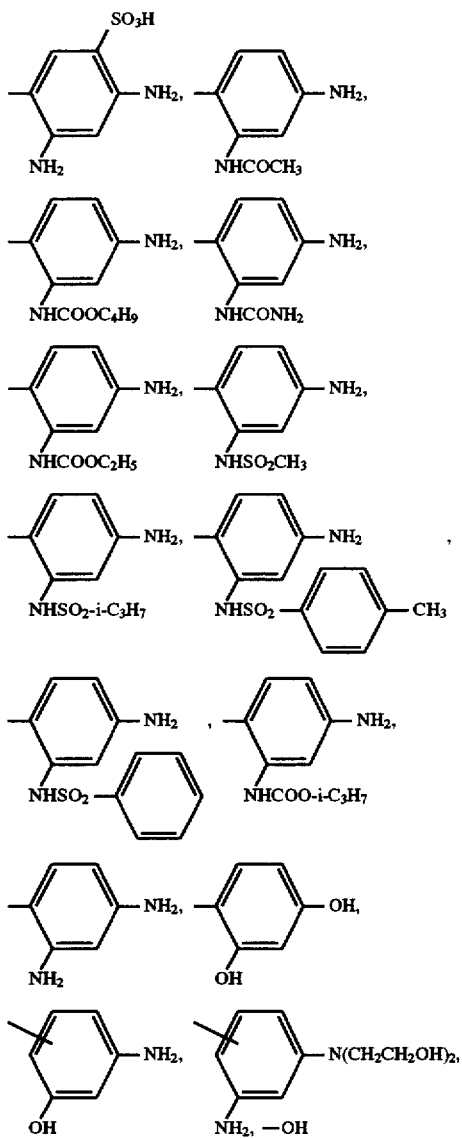

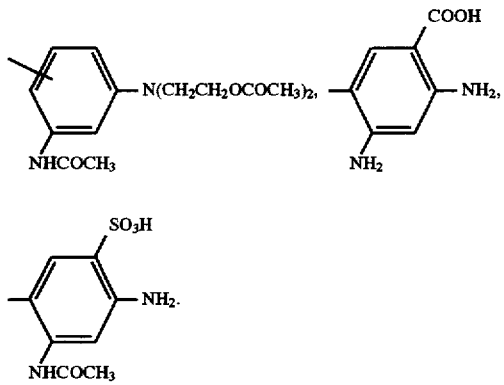

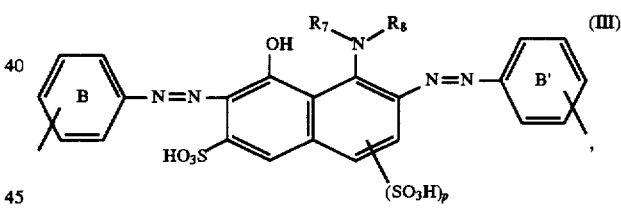

Particular preference is given to radicals of the formula (II) in which m denotes 1 and the remaining radicals have the broadest meaning given above.

Very particular preference is given to polyazo dyestuffs in which A' is A, R$^{1'}$ is R$^1$, R$^{2'}$ is R$^2$, R$^{3'}$ is R$^3$ and X' is X.

Preferred radicals of the tetrazo component T have the formula (III)

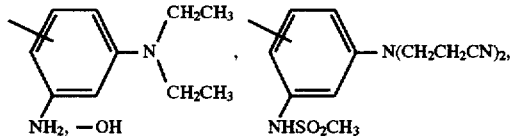

in which

R$^7$ and R$^8$, independently of one another, denote hydrogen or substituted or unsubstituted C$_1$–C$_4$-alkyl, possible substituents preferably being the ones already mentioned above for alkyl radicals, rings B and B', independently of one another, either do not carry any further substituents or carry further substituents, preferred substituents being C$_1$–C$_4$-alkyl, C$_1$–C$_4$-alkoxy, halogen, SO$_3$H and/or COOH, and p denotes 0 or 1.

Radicals of the tetrazo component T which are also preferred have the formula (IV)

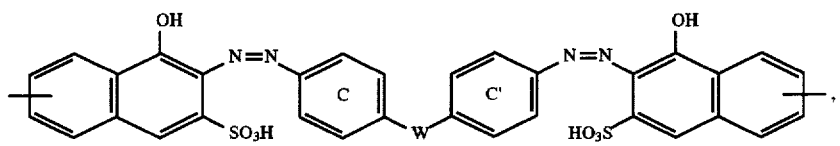

in which rings C and C', independently of one another, either do not carry any further substituents or carry further substituents, preferred substituents being $C_1$-$C_4$-alkyl, $C_1$-$C_4$-alkoxy, halogen, $SO_3H$ and/or COOH, and W represents a bridging member.

Preferred bridging members for W include:

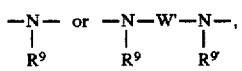

in which W' represents a radical of the formula

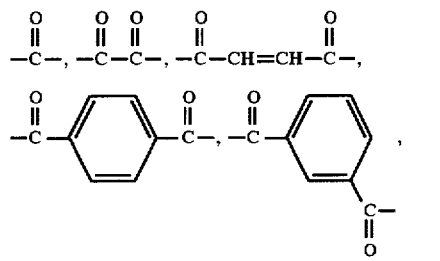

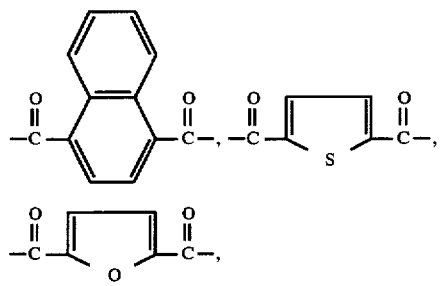

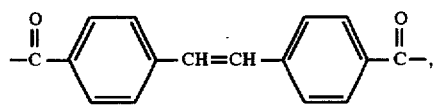

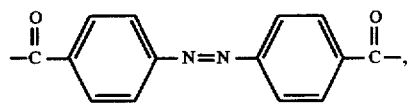

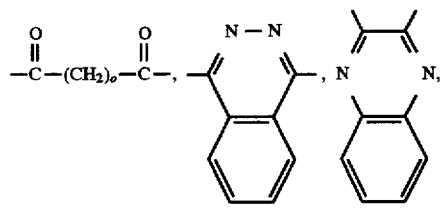

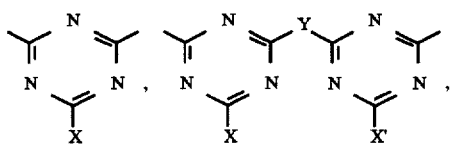

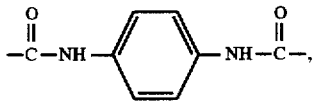

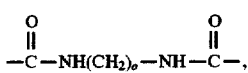

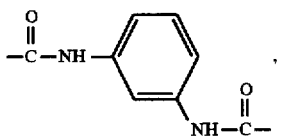

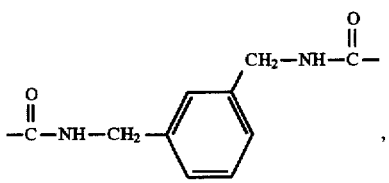

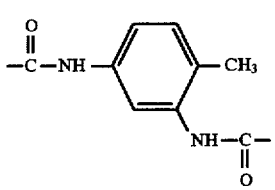

$R^9$ and $R^{9'}$, independently of one another, represent hydrogen or substituted or unsubstituted $C_1$-$C_4$-alkyl, Y represents a bridging member, o is 1 to 6 and X and X', independently of one another, have the meaning given above.

Examples of Y include

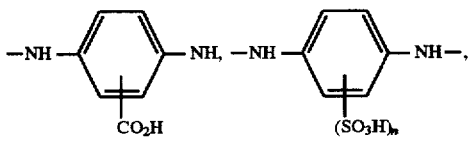

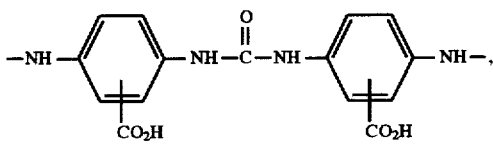

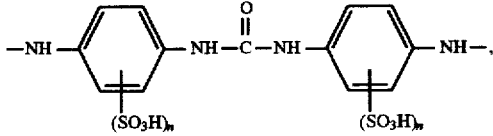

-continued

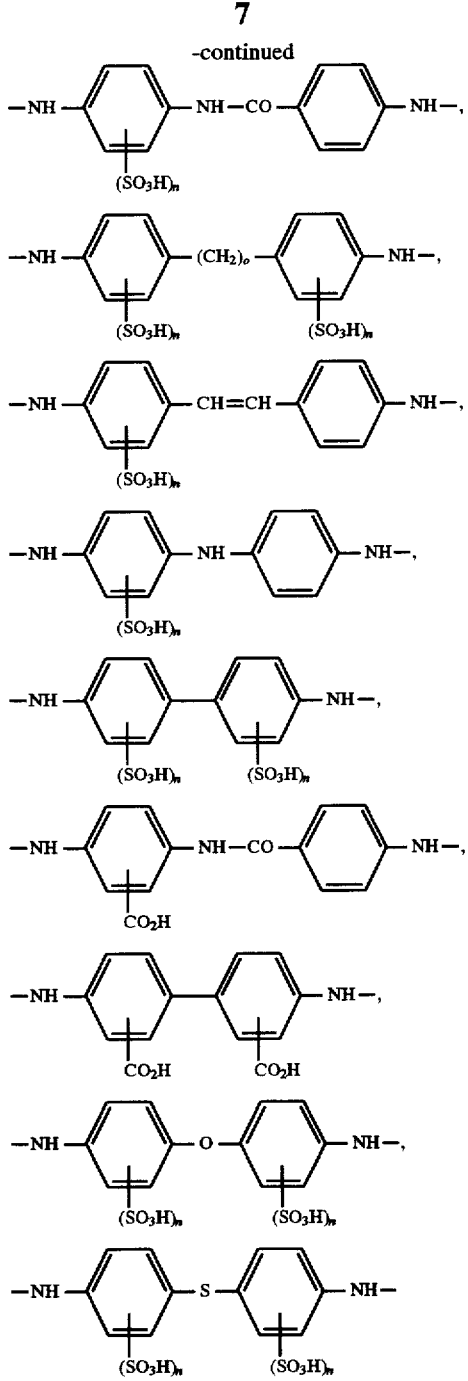

in which o represents 1 to 6 and
n represents 0 or 1.

Preferred radicals denoting

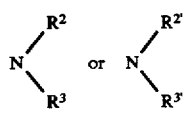

include the radicals of the formulae below

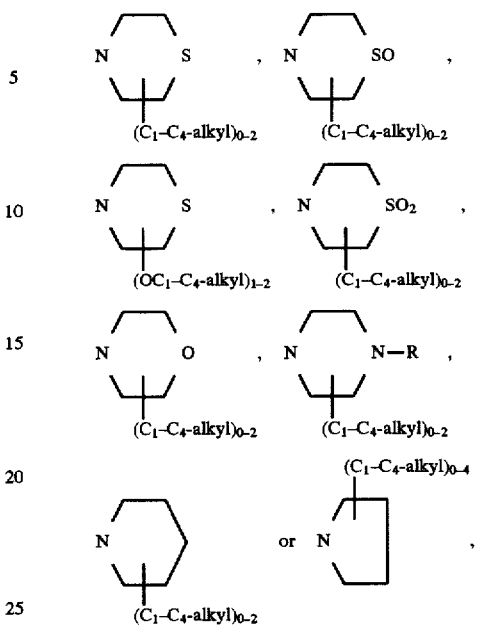

in which

R has the broadest meaning given above or denotes $NHCH_3$, $N(CH_3)_2$, $N(C_2H_5)_2$, $NHC_2H_5$, $NHCH_2CH_2OH$, $NHCH_2CH_2OCH_3$, $N(C_2H_4OH)_2$,

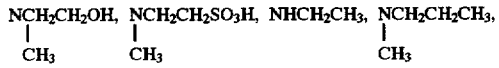

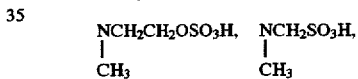

$UNCH_2CH_2OSO_3H$, $NHCH_2CH_2SO_3H$, $NHCH(CH_3)_2$,

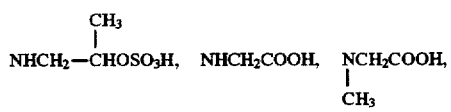

$NHCH_2CH_2COOH$, $N(C_2H_4OSO_3H)_2$, $NH(CH_2)_{10}COOH$, $NH(CH_2CH_2NH)p—CH_2CH_2CH_2$, where p is 0–4, or $NHCH_2CH_2CH_2N(CH_3)CH_2CH_2OH$.

Particularly preferred radicals denoting

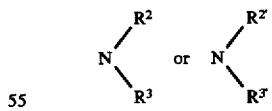

are

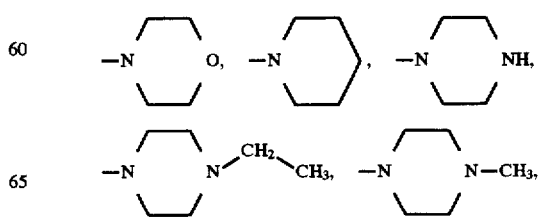

9

-continued

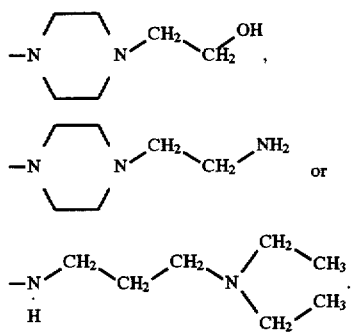

Very particular preference is given to dyestuffs of the formula (I) having the formula (V)

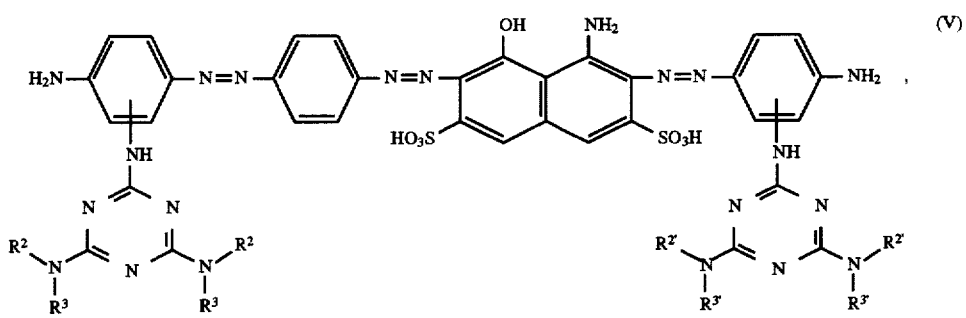

in which
- $R^2$ and $R^3$ and $R^{2'}$ and $R^{3'}$ together with the particular N atom to which they are bonded form, in each case independently of one another, a saturated or unsaturated 3- to 8-membered, in particular 5- or 6-membered, ring which does not contain any further heteroatoms or contains 1 to 2 further heteroatoms from the group consisting of O, S, $SO_2$, SO or NR, where R is H or substituted or unsubstituted $C_4$–$C_6$-alkyl, and is unsubstituted or substituted by $C_1$–$C_4$-alkyl, $C_1$–$C_4$-alkoxy, $C_1$–$C_4$-hydroxyalkyl or $C_1$–$C_4$-aminoalkyl, or
- $R^2$ and $R^{2'}$, independently of one another, represent hydrogen or substituted or unsubstituted $C_1$–$C_4$-alkyl and
- $R^3$ and $R^{3'}$, independently of one another, denote substituted or unsubstituted $C_1$–$C_4$-alkyl.

A very particularly preferred dyestuff of the formula (V) has the formula (VI)

10

The invention furthermore provides a process for preparing dyestuffs of the formula (I), which process is characterized by tetrazotization of the diamines of the formula (VII)

$$H_2N-T-NH_2 \quad (VII)$$

and coupling of the resulting tetrazonium salts onto coupling components of the formula

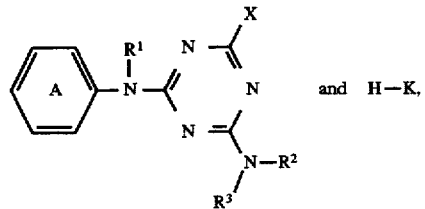

and H—K, in which $R^1$, R2, $R^3$, A, X, T and K have the broadest above meaning Coupling can be carried simultaneously or in succession with coupling components of the formula

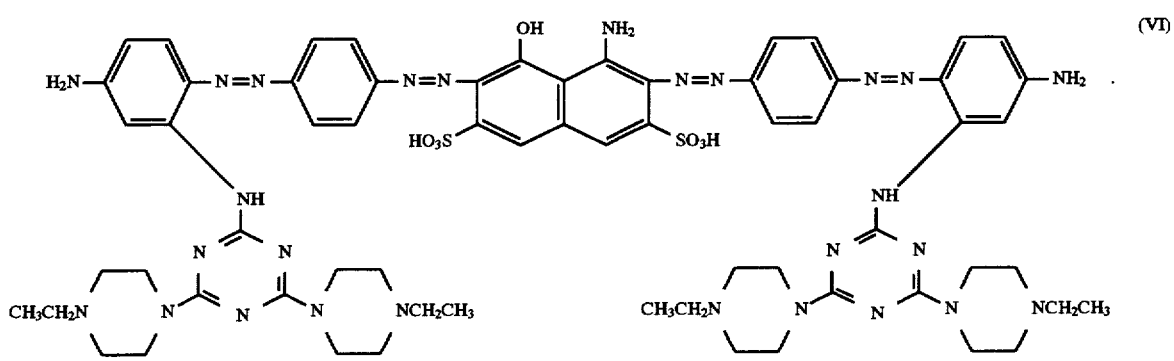

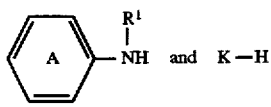 and K—H and the reaction product thereof can then be reacted with a reactive component of the formula

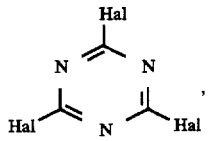

in which Hal represents Cl, F or Br, in particular Cl, and then with HX and

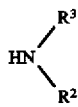

in any desired order.

In the case where K denotes a radical of the formula (II) in which m is 1, coupling can also take place with a coupling, component of the formula

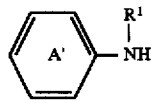

and the resulting product can then be reacted with a reactive component of the formula

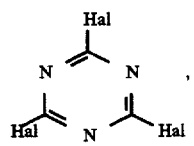

in which

Hal represents Cl, Br or F and then with HX and $HNR^2R^3$ in any desired order.

The coupling reaction preferably takes place in the presence of acid scavengers.

Examples of suitable acid scavengers are alkali metal compounds and alkaline earth metal compounds, such as LiOH, NaOH, KOH, Ca(OH)$_2$, Na$_2$CO$_3$, NaHCO$_3$, Li$_2$CO$_3$.

The coupling component of the formula

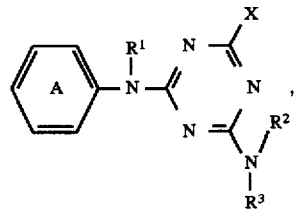

in which the substituents have the meaning given above, can be prepared by condensing compounds of the formula

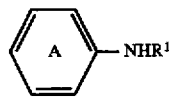

with cyanuric halides, in particular cyanuric chloride, and compounds of the formula H-X and $HNR^2R^3$ in any desired order. The coupling component H-K of the formula

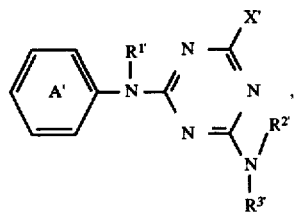

can be prepared analogously.

In the case where ring A or A' carries an $NO_2$ or NHCO-alkyl substituent, it is sensible to carry out a reduction or hydrolysis prior to coupling.

In a preferred embodiment of the process according to the invention, only one coupling component is used, which leads to dyestuffs of the formula (I) containing two identical ends. This coupling component has the formula

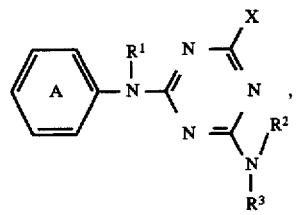

in which $R^1$ to $R^3$, X and A have the meanings given above.

However, compounds of the formula (I) containing different ends can also be prepared by the process according to the invention, for example by the so-called mixed coupling reaction with different coupling components.

The invention furthermore provides compounds of the formula

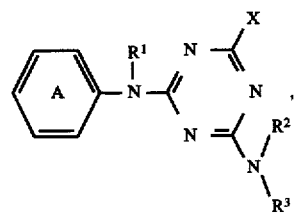

in which $R^1$, $R^2$, $R^3$, A and X have the broadest meaning given above.

The compounds of the formula (I) are preferably used as dyestuffs for dyeing and printing hydroxyl- and/or amido-containing substrates and dye cellulose-containing materials in black hues, in particular paper, cotton and viscose and leather, the colourations or dyeings obtained exhibiting good wet and light fastness properties.

The dyestuffs can be used in accordance with any of the methods customary in the paper and textile industries for substantive dyestuffs, in particular in mass and surface colouration of paper for sized or unsized types, starting from bleached or unbleached pulp of different origins, such as softwood or hardwood sulphite pulp and/or softwood or hardwood sulphate pulp. They can also be used in yarn- and piece-dyeing of cotton, viscose and linen by the exhaust method from a long liquor or in continuous processes.

The invention also provides a process for dyeing cellulose-containing materials with the dyestuffs of the formula (I).

The compounds of the formula (I) according to the invention can be used as solid or liquid dyestuff preparations. They are preferably used in the form of aqueous preparations, in particular of solutions. In general, these aqueous dyestuff preparations contain one or more dyestuffs of the formula (I) and, if desired, suitable organic solvents, which may also include hydrotropic compounds, and further auxiliaries and/or stabilizers. It is advantageous to prepare the dyestuff solutions during the dyestuff synthesis itself, without intermediate isolation of the dyestuff.

Aqueous dyestuff preparations are the preferred form of application, especially when colouring or printing paper. A stable, aqueous concentrated dyestuff preparation can be prepared in a general manner by dissolving the dyestuff in water, if desired with the addition of one or more auxiliaries, for example of a hydrotropic compound or of a stabilizer.

The aqueous dyestuff preparations typically contain about 0.5 to 20% by weight of one or more dyestuffs of the formula (I) and 80 to 99.5% by weight of water and/or solvents and, if desired, further customary components.

Preferred organic solvents are alcohols and ethers thereof or esters, carboxamides, ureas, sulphoxides and sulphones, in particular those having molecular weights <200. Examples of particularly suitable solvents are methanol, ethanol, propanol, ethylene glycol, propylene glycol, diethylene glycol, thiodiethylene glycol and dipropylene glycol; butanediol; β-hydroxypropionitrile, pentamethylene glycol, ethylene glycol monoethyl ether and ethylene glycol monopropyl ether, ethylene diglyclol monoethyl ether, triethylene glycol monobutyl ether, butylpolyglycol, formamide, triethylene glycol, 1,5-pentanediol, 1,3,6-hexanetriol, 2-hydroxyethyl acetate, glycerol, 1,2-dihydroxypropane, 1-methoxy-2-propanol, 2-methoxy- 1-propanol, N,N-dimethylformamide, pyrrolidone, N-methyl-caprolactam, ε-capro-lactam, butyrolactone, urea, tetramethylurea, 1,3-dimethyl-2-imidazolidinone, N,N'-dimethylolpropyleneurea, dimethyl sulphoxide, dimethyl sulphone, sulpholane, isopropanol, polyethylene glycol.

Further suitable additives customary for aqueous dyestuff preparations, in particular for printing inks, are those ionic and nonionic substances by means of which the viscosity and/or the surface tension can be adjusted to the ranges necessary for the application, such as, for example, anionic, cationic or neutral surfactants, such as dispersing agents and viscosity regulators. The function of viscosity regulators can, for example, be performed by the organic solvents.

The dyestuff preparations according to the invention can also contain further dyestuffs not having the formula I. An example of these is Food Black 2.

Preference is given to aqueous dyestuff preparations, in particular dyestuff solutions, containing 0.5 to 20% by weight, in particular 1 to 15% by weight, of one or more dyestuffs, at least one of which has the formula I, 50 to 99.5% by weight, in particular 85 to 99% by weight, of water, 0 to 30% by weight, in particular 0 to 20% by weight, of one or more organic solvents, 0 to 30% by weight, in particular 0 to 10% by weight, of additives affecting the viscosity and/or surface tension, the sum of the ingredients mentioned adding up to 100% by weight.

The aqueous dyestuff preparations can be prepared by dissolving the dyestuff salts in water or from the condensation solutions which, if necessary, are subjected to isomeric exchange and/or desalting, for example by pressure permeation, and/or by adding one or more of the abovementioned organic solvents, if desired at elevated temperatures (30 to 100° C., in particular 30 to 50° C.) and adding inorganic and organic bases. If desired, the additional use of customary ionic or nonionic additives is also possible, for example of those by means of which the viscosity can be lowered and/or the surface tension raised.

Instead of the salts of (I), the corresponding free acids can be used in combination with at least equimolar amounts of the corresponding inorganic or organic bases.

The inorganic bases used can be, for example, lithium hydroxide, sodium hydroxide, potassium hydroxide, lithium carbonate, sodium carbonate, potassium carbonate.

Examples of compounds which can serve as organic bases include ethanolamine, diethanolamine, triethanolamine, N-methylethanolamine, N,N-dimethylethanol-amine, N-methyldiethanolamine, 1-amino-2-propanol, 2-amino-1-propanol, di-iso-propanolamine, N-2-hydroxyethyl-diisopropanolamine, N,N,N-tris-[2-(2'-hydroxy-ethoxy)-ethyl]-amine or sodium methoxide, lithium methoxide, potassium tertbutoxide.

The aqueous dyestuff preparations according to the invention are also suitable for preparing printing inks which can be used, in particular, as recording fluids in the ink-jet method.

Accordingly, the invention also relates to printing inks containing at least one dyestuff (I) and to their use as recording fluid for ink-jet recording systems for the purpose of producing black prints.

The ink-jet method of the process according to the invention refers to an ink-jet recording method in which the ink droplets are sprayed onto the substrate. The fine ink droplets can be generated by various methods. Preferably, they are produced by the generally known thermal-jet, bubble-jet, piezo-jet or valve-ink-jet methods.

Using the dyestuffs according to the invention in the form of their aqueous preparations, in particular of their printing inks, as recording fluid for ink-jet recording systems offers the following advantages: the physical properties, such as viscosity, surface tension and the like, are in the suitable ranges; the recording fluid does not lead to clogging in fine outlet nozzles of ink-jet recording apparatuses; it produces images of high density; during storage no change in the physical properties and no deposition of solid components take place in the recording fluid; the recording fluid is suitable for recording on various recording media without restriction as to the type of recording media; finally, the recording fluid is fixed rapidly and gives images having excellent water fastness, light fastness, wear resistance and resolution.

The preparation examples which follow serve to illustrate the present invention without, however, limiting it thereto. In the examples, parts are always by weight, unless stated otherwise.

The dyeings and prints obtained with the dyestuffs according to the invention, in particular the prints obtained on paper by the ink-jet method, exhibit excellent wet fastness properties.

EXAMPLES

EXAMPLE 1

0.55 mol of cyanuric chloride was dissolved in 500 ml of acetone, and 0.5 mol of 1-amino-3-nitrobenzene was added in portions over a period of 20 minutes at 0 to 5° C., and the resulting mixture was stirred for another 30 minutes. 100 ml of 20% strength sodium carbonate solution were then added, the mixture was again stirred for 1 hour at 0° C. and then poured onto 1 l of ice-water. The precipitate was filtered off with suction, thoroughly pressed and washed with 0.5 l of ice-water. The residue was introduced into excess 2-hydroxyethyl-piperazine, which resulted in an increase of the temperature to 105° C. The mixture was stirred for 1 hour at 100° C., cooled overnight, poured into ice-water, the precipitate was filtered off with suction, washed with ice-water and thoroughly pressed. The residue was dissolved in 750 ml of ethanol and hydrogenated with Raney nickel in an autoclave at 50° C. until the pressure remained constant. The catalyst was filtered off, the filtrate was concentrated, the residue was taken up in water, and the product was dissolved with hydrochloric acid to give the coupling component of the formula

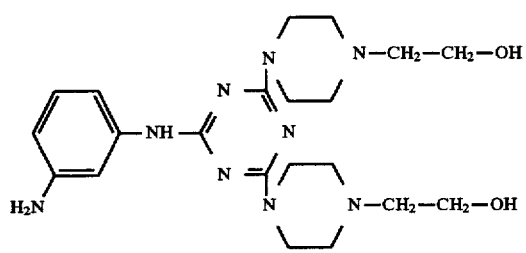

Replacing the 2-hydroxyethylpiperazine in Example 1 by the following amines of Table 1 gave other important coupling components of the formula

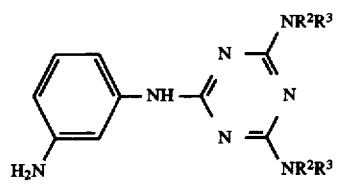

TABLE 1

| Example | HNR²R³ |
|---------|--------|
| 2 | H—N⟨piperazine⟩N—CH₃ |
| 3 | H—N⟨piperazine⟩N—CH₂—CH₃ |
| 4 | H—N⟨piperazine⟩N—CH₂—CH₂—NH₂ |
| 5 | H—N⟨morpholine⟩O |
| 6 | H₂N—CH₂—CH₂—CH₂—N(CH₃)₂ |
| 7 | H₂N—CH₂—CH₂—CH₂—N(CH₂CH₃)₂ |

EXAMPLE 8

0.07 mol of the compound of the formula

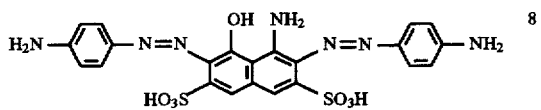

was stirred in 250 ml of water, the resulting mixture was brought to a pH of 8 with sodium carbonate, NaNO₂ solution was added, and the mixture was added dropwise to a solution of 120 ml of HCl and 250 g of ice and diazotized. After stirring the mixture for 1 hour in the presence of excess nitrite, the excess nitrite was destroyed with sulfamic acid. 0.15 mol of the coupling component of the formula (I) was then added to this diazotization reaction mixture, the pH was brought to 4.5 with solid sodium acetate, and the mixture was stirred for 2 hours. It was then brought to a pH of 8 with sodium carbonate solution, stirred overnight, the precipitate was filtered off with suction, washed with water and dried to give the dyestuff of the formula

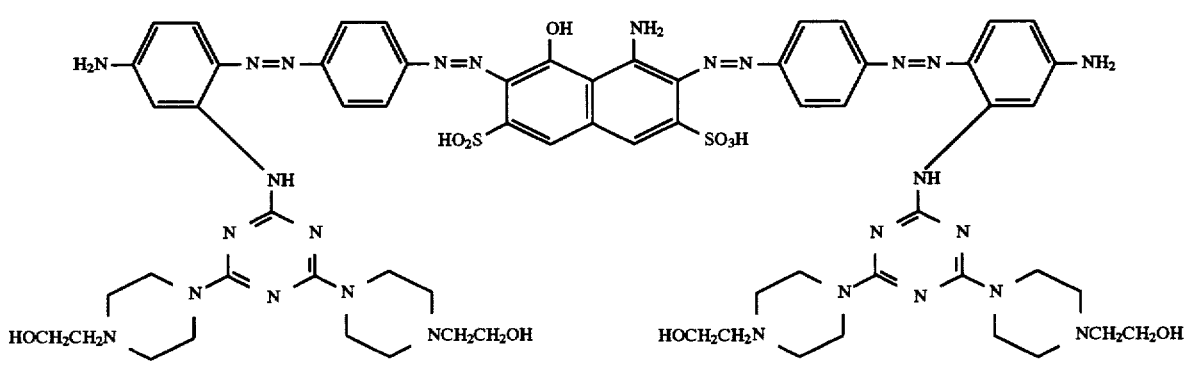

which colours paper in green-black hues.

Replacing the coupling component from Example 1 in Example 8 by a coupling component from Table 1 gave other valuable dyestuffs of the formula

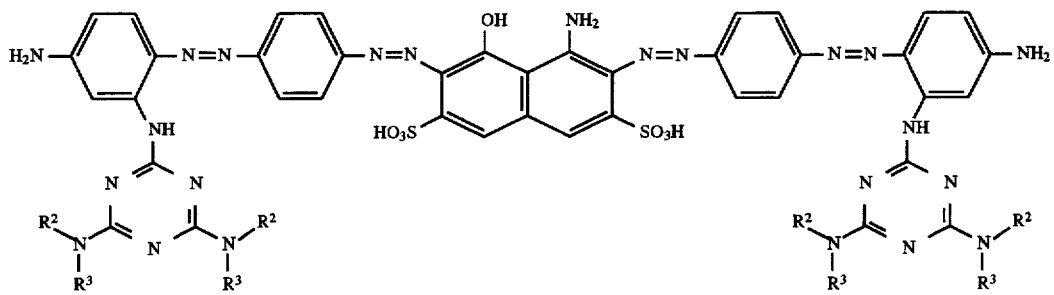

which are listed in Table 2.

TABLE 2

| Example | Coupling component from Example |
|---------|--------------------------------|
| 9  | 2 |
| 10 | 3 |
| 11 | 4 |
| 12 | 5 |
| 13 | 6 |
| 14 | 7 |

EXAMPLES 15 TO 21

Replacing the compound of the formula 8 in Examples 8 to 14 by the compound of the formula

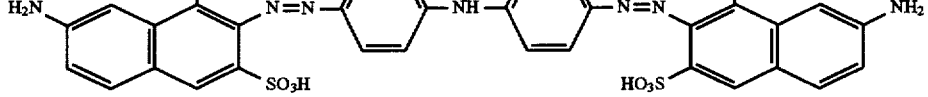

gave dyestuffs of the formula

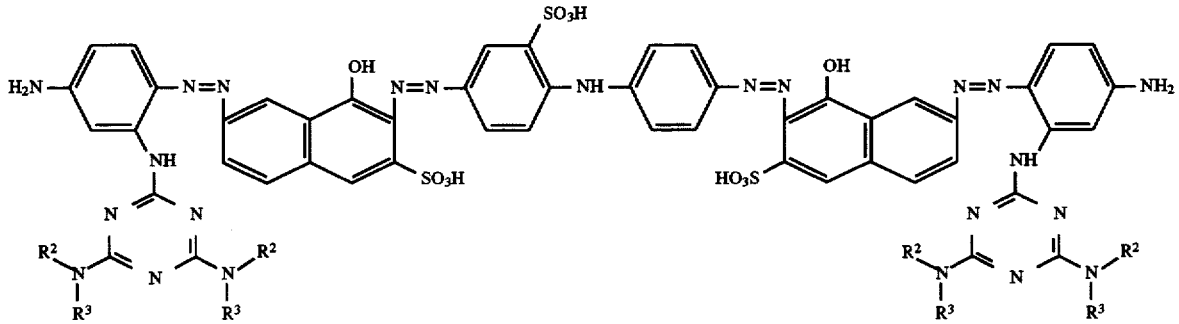

which are listed in Table 3 and which coloured paper in bluish black hues.

TABLE 3

| Example | Coupling component from Example |
|---------|--------------------------------|
| 15 |  1 (HNR$^2$R$^3$ $\underline{\Delta}$ H—N  N—CH$_2$—CH$_2$—OH) |
| 16 | 2 |
| 17 | 3 |
| 18 | 4 |
| 19 | 5 |
| 20 | 6 |
| 21 | 7 |

EXAMPLE 22

0.29 mol of metaminic acid was suspended in water, dissolved by means of NaOH, and the resulting solution was rapidly poured into 0.3 mol of cyanuric chloride in ice-water. The pH was maintained at 4 to 4.5 with sodium carbonate solution, and stirring of the mixture was continued for 1 hour at 15° C. The condensation product was then separated off and introduced into excess N-ethylpiperazine/ ice-water. The solution heated up to 45° C. and was then further heated to 95° C. and stirred for 1 hour. Cooling led to precipitation of the product of the formula

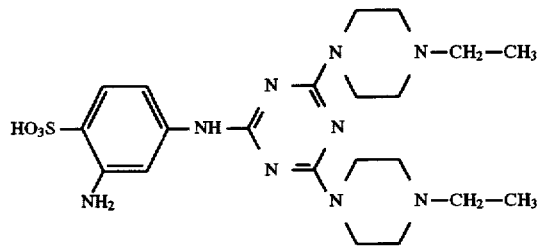

which was filtered off with suction and dried.

Replacing N-ethylpiperazine in Example 22 by the amines from Table 4 gave further important coupling components of the formula

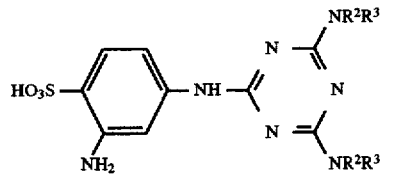

TABLE 4

| Example | Amine H—N $R^2R^3$ |
|---|---|
| 23 | H—N⌒N—CH₃ |
| 24 | H—N⌒N—CH₂—CH₂—OH |
| 25 | H—N⌒N—CH₂—CH₂—NH₂ |

TABLE 4-continued

| Example | Amine H—N $R^2R^3$ |
|---|---|
| 26 | H—N⌒O |
| 27 | H₂N—CH₂—CH₂—CH₂—N(CH₃)₂ |
| 28 | H₂N—CH₂—CH₂—CH₂—N(CH₂CH₃)₂ |

EXAMPLES 29 TO 35

Replacing the coupling component of the formula 1 in Example 8 by the coupling components from Examples 22 to 28 gave the dyestuffs of the formula

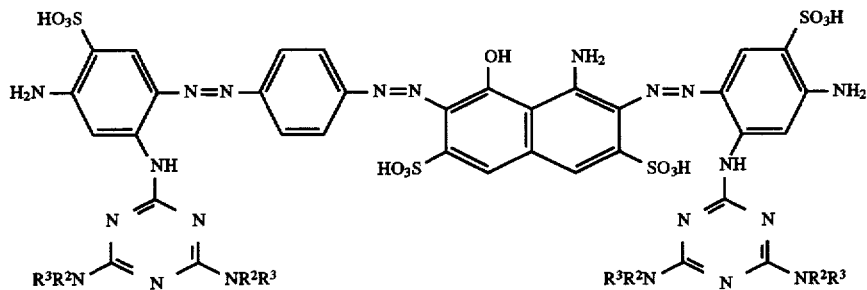

which are listed in Table 5 and which likewise colour paper in black hues.

TABLE 5

| Example | Coupling component from Example |
|---|---|
| 29 | 22 (HNR²R³ ≙ H—N⌒N—CH₂—CH₃) |
| 30 | 23 |
| 31 | 24 |
| 32 | 25 |
| 33 | 26 |
| 34 | 27 |
| 35 | 28 |

EXAMPLES 36 TO 42

Replacing the tetrazo component in Examples 29 to 35 by that from Example 15 gave the compounds of the formula

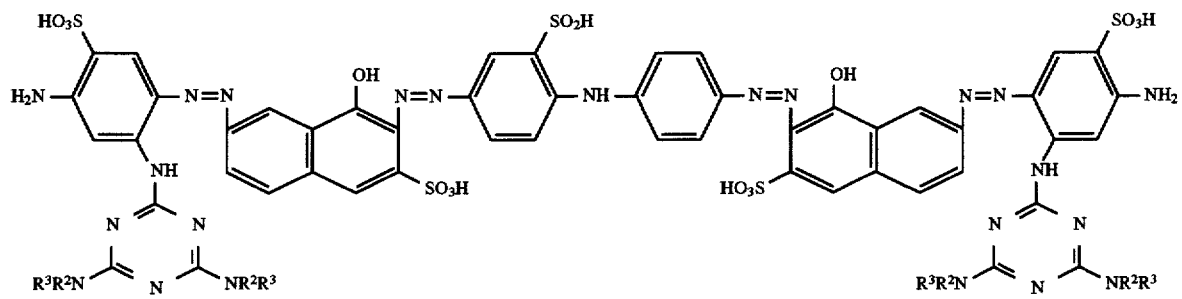

which are listed in Table 6

TABLE 6

| Example | Coupling component from Example |
|---|---|
| 36 | 22 (HNR²R³ ≙ H—N⟨  ⟩N—CH₂—CH₃) |
| 37 | 23 |
| 38 | 24 |
| 39 | 25 |
| 40 | 26 |
| 41 | 27 |
| 42 | 28 |

EXAMPLES 43 TO 56

Replacing the tetrazo component of the formula 8 in Examples 8 to 14 and 29 to 35 by the compound of the formula

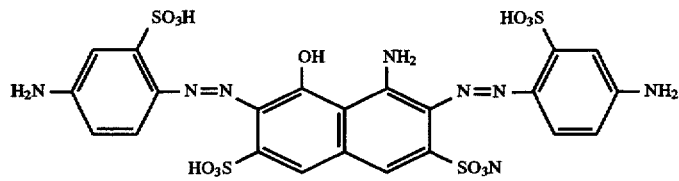

which is prepared by acid coupling of oxalylparaminic acid in the presence of urea, followed by alkaline coupling of oxalylparaminic acid and alkaline hydrolysis of the oxalyl groups, gave dyestuffs of the formula

TABLE 7

| Example | Coupling component from Example | Substituent |
|---|---|---|
| 43 | 1 (HNR²R³ ≙ HN⟨  ⟩N—CH₂—CH₂—OH) | H |
| 44 | 2 | H |
| 45 | 3 | H |
| 46 | 4 | H |
| 47 | 5 | H |
| 48 | 6 | H |
| 49 | 7 | H |
| 50 | 22 (HNR²R³ ≙ HN⟨  ⟩N—CH₂—CH₃) | SO₃H |
| 51 | 23 | SO₃H |

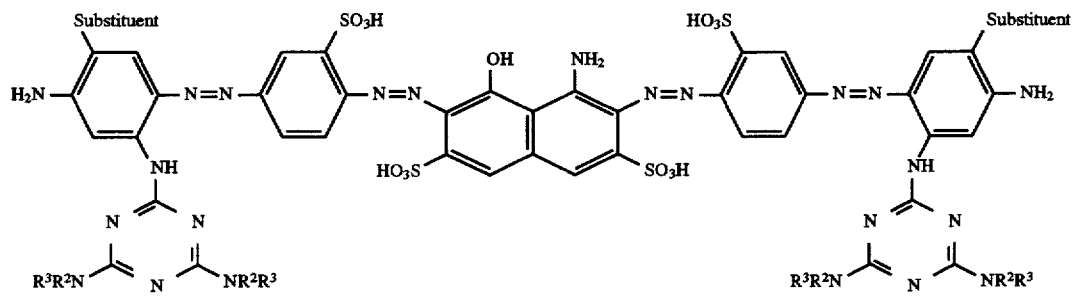

which are listed in Table 7 and which colour paper in bluish black hues.

TABLE 7-continued

| Example | Coupling component from Example | Substituent |
|---|---|---|
| 52 | 24 | SO₃H |
| 53 | 25 | SO₃H |
| 54 | 26 | SO₃H |
| 55 | 27 | SO₃H |
| 56 | 28 | SO₃H |

EXAMPLES 57 TO 70

Replacing the tetrazo component 43 in Examples 43 to 56 by the compound of the formula 57

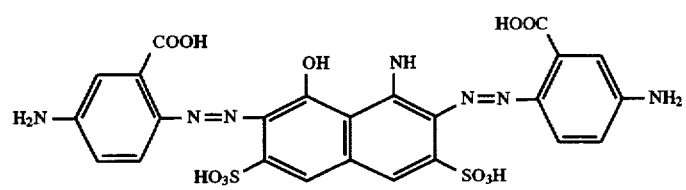

which is prepared by acid and alkaline coupling of 5-nitro-2-aminobenzoic acid onto H acid, followed by reduction with NaHS, gave dyestuffs of the formula

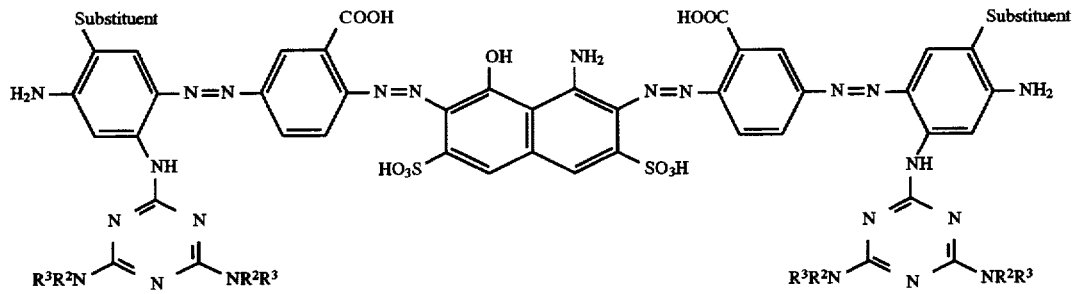

which are listed in Table 8 and which colour paper in bluish black hues.

TABLE 8

| Example | Coupling component from Example | Substituent |
|---|---|---|
| 57 | 1 (HNR²R³ ≙ HN⟨ ⟩N—CH₂—CH₂—OH) | H |
| 58 | 2 | H |
| 59 | 2 | H |
| 60 | 4 | H |
| 61 | 5 | H |
| 62 | 6 | H |
| 63 | 7 | H |
| 64 | 22 (HNR²R³ ≙ HN⟨ ⟩N—CH₂—CH₃) | SO₃H |
| 65 | 23 | SO₃H |
| 66 | 24 | SO₃H |
| 67 | 25 | SO₃H |

TABLE 8-continued

| Example | Coupling component from Example | Substituent |
|---|---|---|
| 68 | 26 | SO₃H |
| 69 | 27 | SO₃H |
| 70 | 28 | SO₃H |

EXAMPLES 71 TO 84

Replacing the tetrazo component 57 in Examples 57 to 70 by the compound of the formula 71

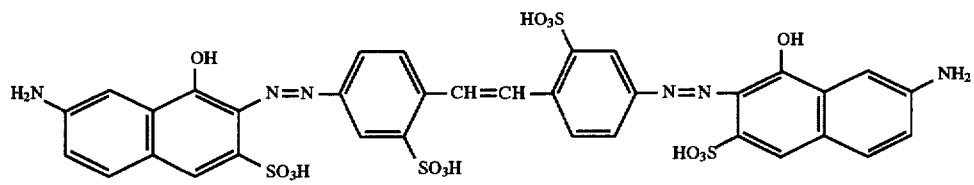

gave dyestuffs of the formula

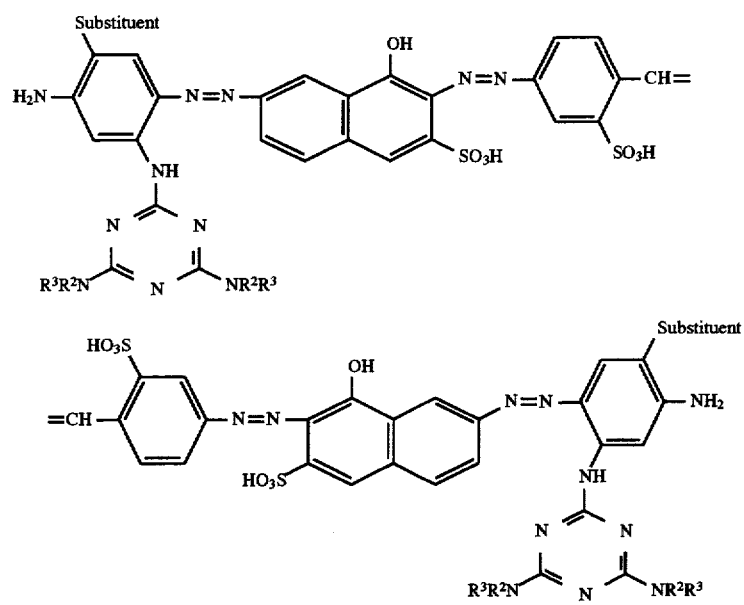

which are listed in Table 9 and which coloured paper in greenish black hues.

TABLE 9

| Example | Coupling component from Example | Substituent |
|---|---|---|
| 71 | 1 (HNR²R³ ≙ H—N⟨ ⟩N—CH₂—CH₂—OH) | H |
| 72 | 2 | H |
| 73 | 3 | H |
| 74 | 4 | H |
| 75 | 5 | H |
| 76 | 6 | H |
| 77 | 7 | H |
| 78 | 22 (HNR²R³ ≙ H—N⟨ ⟩N—CH₂—CH₃) | SO₃H |
| 79 | 23 | SO₃H |
| 80 | 24 | SO₃H |
| 81 | 25 | SO₃H |
| 82 | 26 | SO₃H |
| 83 | 27 | SO₃H |
| 84 | 28 | SO₃H |

We claim:

1. A compound of the formula (I)

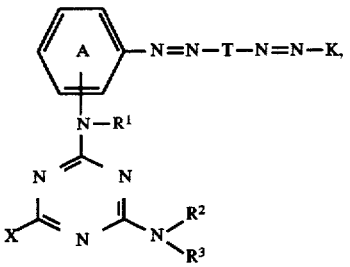

in which

T represents the radical of a tetrazo component, $R^1$ denotes hydrogen or substituted or unsubstituted $C_1-C_4$-alkyl, $R^2$ and $R^3$ together with the N atom to which they are bonded form a saturated or unsaturated 3- to 8-membered ring containing no further heteroatoms or containing 1 or 2 further heteroatoms selected from the group consisting of O, S, SO, SO₂ and NR, where R is H or substituted or unsubstituted $C_1-C_6$-alkyl, which is unsubstituted or substituted by $C_1-C_4$-alkyl, $C_1-C_4$-alkoxy, $C_1-C_4$-hydroxyalkyl or $C_1-C_4$-aminoalkyl, X represents $NR^2R^3$ ring A is unsubstituted or further substituted with one or more members of the group consisting of $C_1-C_4$-alkyl, $C_1-C_4$-alkoxy, halogen, OH, S—$C_1-C_4$-alkyl, $NR^4R^5$ wherein $R^4$ and $R^5$, independently of one another represent hydrogen, or $C_1$-$C_4$-alkyl which is unsubstituted or substituted by one or more water solubilizing groups selected from the group consisting of $SO_3H$, $OSO_3H$, and COOH; $SO_3H$, COOH, —$NR^1COC_1$-$C_4$-alkyl, $NR^1COC_6$-$C_{10}$-aryl, —$NR^1$—$SO_2$—$C_1$-$C_4$-alkyl, $NR_1$—$SO_2$—$C_6$-$C_{10}$-aryl, —$NR^1CONH_2$, —$NR^1$—$COCH_2OH$, $NR^1COOC_1$-$C_4$-alkyl and $NR^2R^3$ wherein the substituents for the substituted alkyl radicals in the definitions of $R^1$, $R^{1'}$ and R are selected from the group consisting of OH, $C_1$-$C_4$-alkoxy, Cl, F, Br, COOH, $SO_3H$, $OSO_3H$, $NR^4R^5$, $R^4$ and $R^5$ having the meanings given above, and combinations thereof, K denotes a radical of the formula (II)

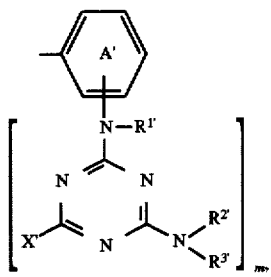

in which m represents 1, $R^{1'}$ denotes hydrogen or substituted or unsubstituted $C_1$-$C_4$-alkyl, $R^{2'}$ and $R^{3'}$ together with the N atom to which they are bonded form a saturated or unsaturated 3- to 8-membered ring containing no further heteroatoms or containing 1 or 2 further heteroatoms selected from the group consisting of O, S, SO, $SO_2$ and NR, where R is H or unsubstituted or substituted $C_1$-$C_4$-alkyl, which is unsubstituted or substituted by $C_1$-$C_4$-alkyl, $C_1$-$C_4$-alkoxy, $C_1$-$C_4$-hydroxyalkyl or $C_1$-$C_4$-aminoalkyl, X' represents $NR^{2'}R^{3'}$ ring A' is not further substituted or is further substituted with one or more members of the group consisting of $C_1$-$C_4$-alkyl, $C_1$-$C_4$-alkoxy, halogen, OH, S—$C_1$-$C_4$-alkyl, $NR^4R^5$ wherein $R^4$ and $R^5$, independently of one another represent hydrogen, or $C_1$-$C_4$-alkyl which is unsubstituted or substituted by one or more water solubilizing groups selected from the group consisting of $SO_3H$, $OSO_3H$, and COOH; $SO_3H$, COOH, —$NR^1COC_1$-$C_4$-alkyl, $NR^1COC_6$-$C_{10}$-aryl, —$NR^1$ —$SO_2$—$C_1$-$C_4$-alkyl, $NR_1$—$SO_2$—$C_6$-$C_{10}$-aryl, —$NR^1CONH_2$, —$NR^1$—$COCH_2OH$, $NR^1COOC_1$-$C_4$-alkyl and $NR^2R^3$ wherein the substituents for the substituted alkyl radicals in the definitions of $R^1$, $R^{1'}$ and R are selected from the group consisting of OH, $C_1$-$C_4$-alkoxy, Cl, F, Br, COOH, $SO_3H$, $OSO_3H$, $NR^4R^5$, $R^4$ and $R^5$ having the meanings given above, and combinations thereof.

2. The compound according to claim 1, in which m is 1, A is A, $R^{1'}$ is $R^1$, $R^{2'}$ is $R^2$, $R^{3'}$ is $R^3$ and X' is X.

3. The compound according to claim 1, in which the radical of the tetrazo component T has the formula (III)

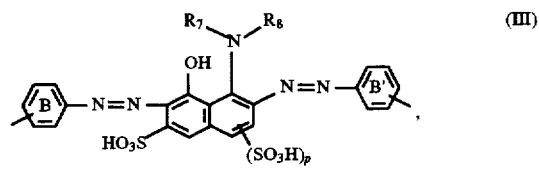

in which $R^7$ and $R^8$, independently of one another, denote hydrogen or substituted or unsubstituted $C_1$-$C_4$-alkyl, rings B and B', independently of one another, either do not carry any further substituents or carry further substituents and p denotes 0 to 1.

4. The compound according to claim 1, in which the radical of the tetrazo component T has the formula (IV)

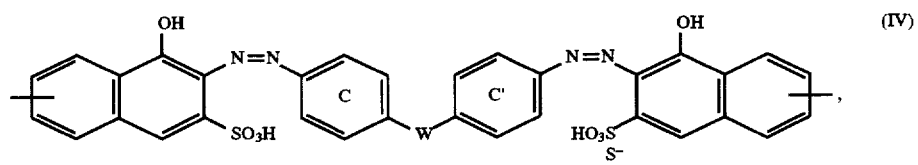

in which rings C and C', independently of one another, either do not carry any further substituents or carry further substituents and w represents

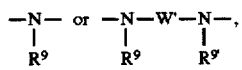

in which W' represents a member of the group consisting of

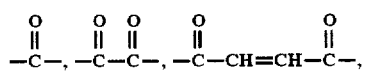

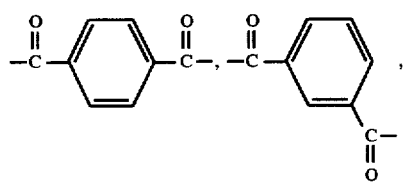

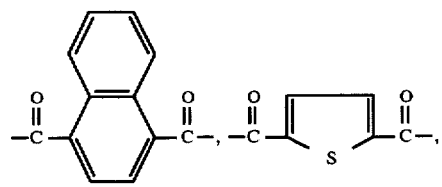

-continued
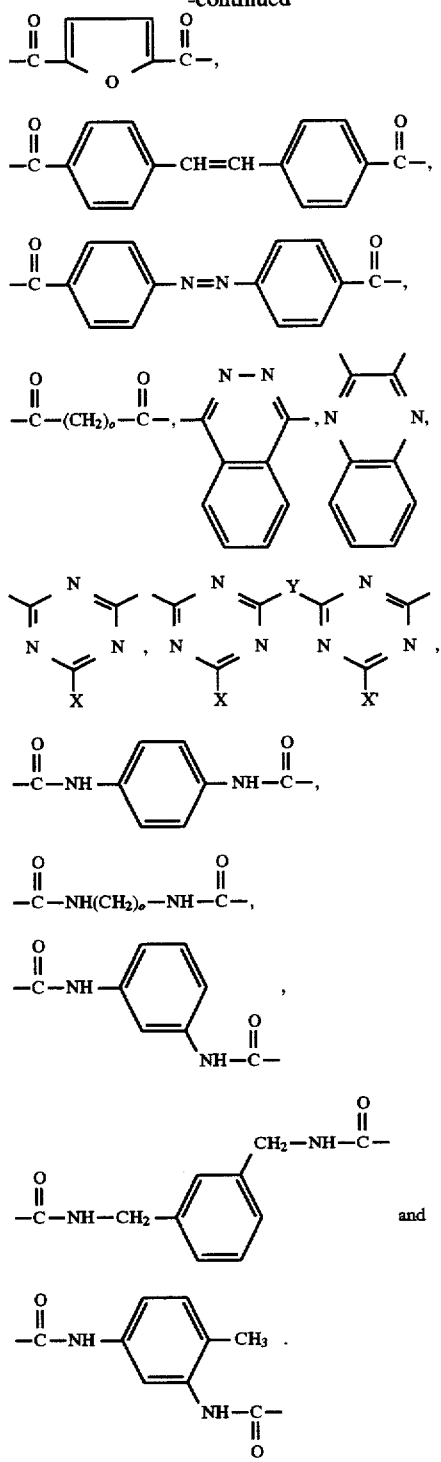
in which
R⁹ and R⁹', independently of one another, represent hydrogen or substituted or unsubstituted $C_1$–$C_4$-alkyl, the substituents being the substituents defined in claim 1,
o is 1 to 6 and
X and X', independently of one another, have the meaning given above,
Y represents a member of the group consisting of
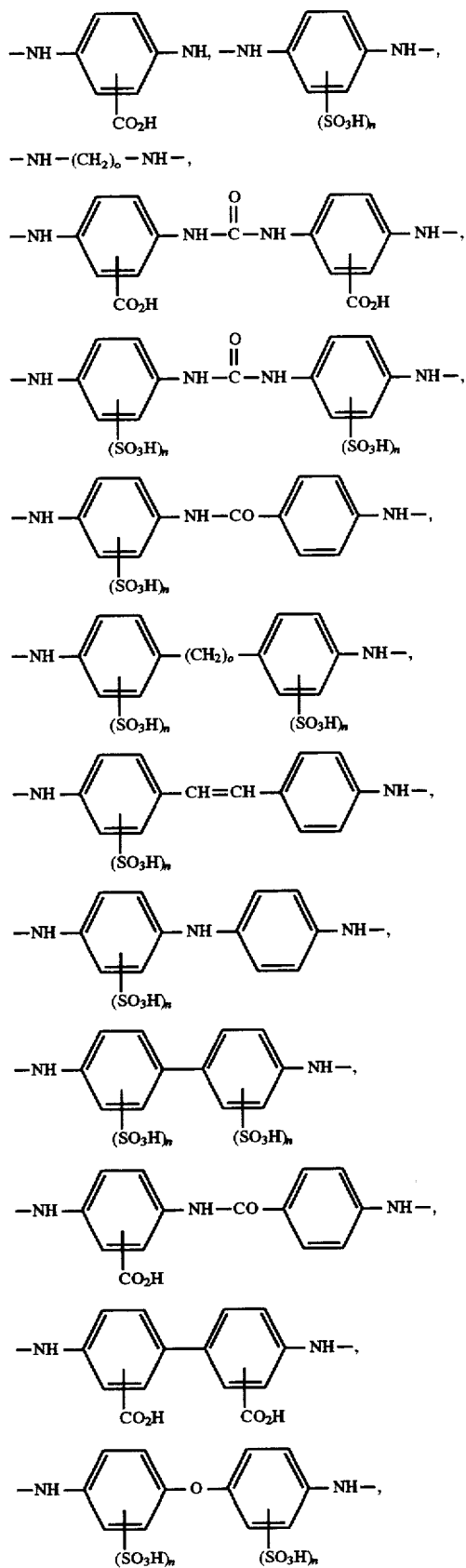

-continued

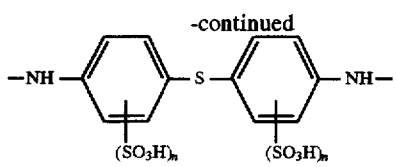

in which
o represents 1 to 6 and
n represents 0 or 1.

5. The compound according to claim 1, in which

denotes a radical of the formula

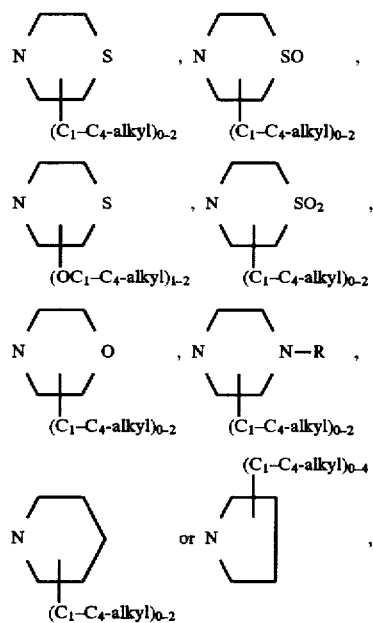

in which
R has the broadest meaning given in claim 1.

6. The compound according to claim 1, having the formula (IV)

7. The compound according to claim 1, wherein $R^2$ and $R^3$ together with the N-atom to which they are bonded form a saturated or unsaturated 5- or 6-membered ring which either does not contain any further heteroatoms or contains 1 to 2 further heteroatoms.

8. The compound according to claim 1, wherein $R^{2'}$ and $R^{3'}$ together with the N-atom to which they are bonded form a saturated or unsaturated 5- or 6-membered ring which either does not contain any further heteroatoms or contains 1 to 2 further heteroatoms.

9. An aqueous dyestuff preparation containing 0.5 to 20% by weight of one or more dyestuffs, at least one of which is a compound according to claim 1, 50 to 99.5% by weight of water, 0 to 30% by weight of one or more organic solvents, 0 to 30% by weight of additives affecting the viscosity and/or surface tension, the sum of the ingredients mentioned adding up to 100% by weight.

10. The aqueous dyestuff preparation according to claim 9 which is a dyestuff solution.

11. A printing ink, containing at least one dyestuff which is a compound according to claim 1.

12. A process for preparing a compound according to claim 1, characterized by tetrazotization of the diamine of the formula (VII)

$$H_2N—T—NH_2 \qquad (VII)$$

and coupling of the resulting tetrazonium salt onto a coupling component of the formula

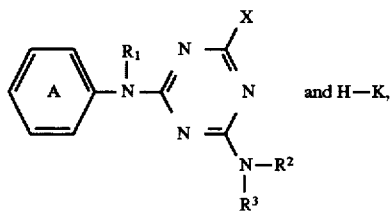

in which
$R^1$, $R^2$, $R^3$, A, X, T and K have the meaning given in claim 1.

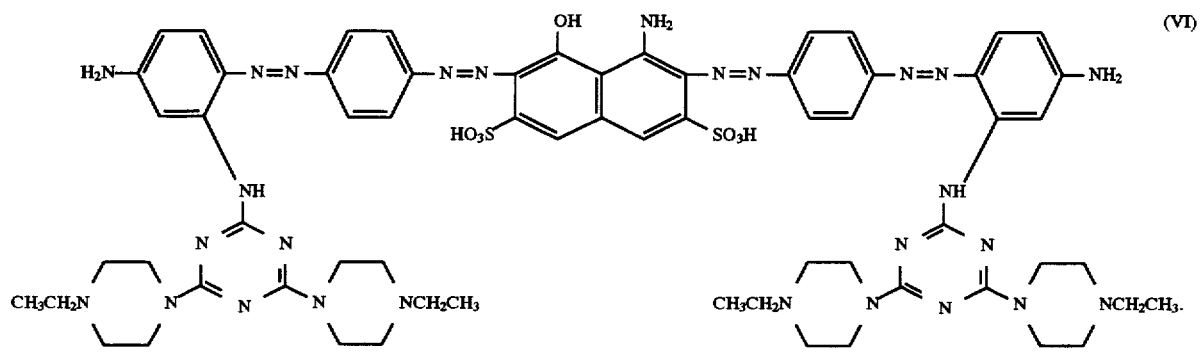

* * * * *